United States Patent
Dastrup

(10) Patent No.: US 11,123,217 B2
(45) Date of Patent: Sep. 21, 2021

(54) REUSABLE, DISCREET ABSORBENT BED PAD

(71) Applicant: Linda L. Dastrup, Orem, UT (US)

(72) Inventor: Linda L. Dastrup, Orem, UT (US)

(73) Assignee: Linda L. Dastrup, Orem, UT (US)

(*) Notice: Subject to any disclaimer, the term of this patent is extended or adjusted under 35 U.S.C. 154(b) by 678 days.

(21) Appl. No.: 15/385,856

(22) Filed: Dec. 20, 2016

(65) Prior Publication Data

US 2018/0168849 A1    Jun. 21, 2018

(51) Int. Cl.
*A61F 5/48* (2006.01)
*A61F 13/15* (2006.01)

(52) U.S. Cl.
CPC ............ *A61F 5/485* (2013.01); *A61F 13/15* (2013.01); *A61F 13/15268* (2013.01); *A61F 2013/15056* (2013.01); *A61F 2013/15154* (2013.01)

(58) Field of Classification Search
CPC .... A61F 5/485; A61F 13/15268; A61F 13/15; A61F 2013/15154; A61F 2013/15056
See application file for complete search history.

(56) References Cited

U.S. PATENT DOCUMENTS

| 4,844,965 A * | 7/1989 | Foxman .................. A61F 5/485 428/91 |
| 5,099,532 A | 3/1992 | Thomas et al. |
| 5,701,617 A * | 12/1997 | Colby .................. A47C 27/006 5/484 |
| 8,161,583 B1 * | 4/2012 | Palen ..................... A61G 7/001 5/81.1 T |
| 2003/0124928 A1 * | 7/2003 | Sherrod ............... A47C 27/006 442/76 |
| 2009/0211030 A1 * | 8/2009 | Norstrem ................. A47G 9/10 5/640 |

FOREIGN PATENT DOCUMENTS

DE       2142732 A1 *  3/1973   ............. A61F 5/485

* cited by examiner

Primary Examiner — David R Hare
Assistant Examiner — Alexis Felix Lopez
(74) Attorney, Agent, or Firm — Kirton McConkie; David Tingey; Alexis Nelson

(57) ABSTRACT

A reusable, discreet absorbent bed pad for medical use. The bed pad may include a base layer and an upper layer. The upper layer may include an aperture to receive an absorbent pad between the base layer and the upper layer such that a central portion of the absorbent pad is exposed through the aperture and an outer periphery of the absorbent pad is overlapped by the upper layer. A weighted blanket for medical use is also disclosed and claimed herein.

10 Claims, 2 Drawing Sheets

REUSABLE, DISCREET ABSORBENT BED PAD

BACKGROUND

Field of the Invention

This invention relates to bed pads for medical use.

Background of the Invention

Urinary incontinence is a common and embarrassing problem that affects a wide variety of people, from children to the elderly. Some individuals may be affected by urinary incontinence only temporarily, such as during pregnancy or childbirth or while undergoing certain medical treatments, while for the bedridden, the physically disabled, or the mentally handicapped, it may be a lifelong struggle.

Bedwetting can be especially traumatic for affected individuals, and may cause them to avoid situations where their problem may be discovered. Sadly, many such people miss out on overnight trips and vacations with friends and family, campouts, summer camps, and the like, just to keep their secret. In addition, regularly soiled sheets cause considerable practical issues and aggravation, requiring substantial time, effort, and money to launder and replace. Odors associated with regular bedwetting may be nearly impossible to remove.

Accordingly, what are needed are methods and systems to reliably protect a mattress and other bedding from soiling due to urinary incontinence or other bodily fluids. Ideally, such systems and methods would be both comfortable and discreet for the user, and would be reusable to reduce costs associated therewith.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

Figure 1:
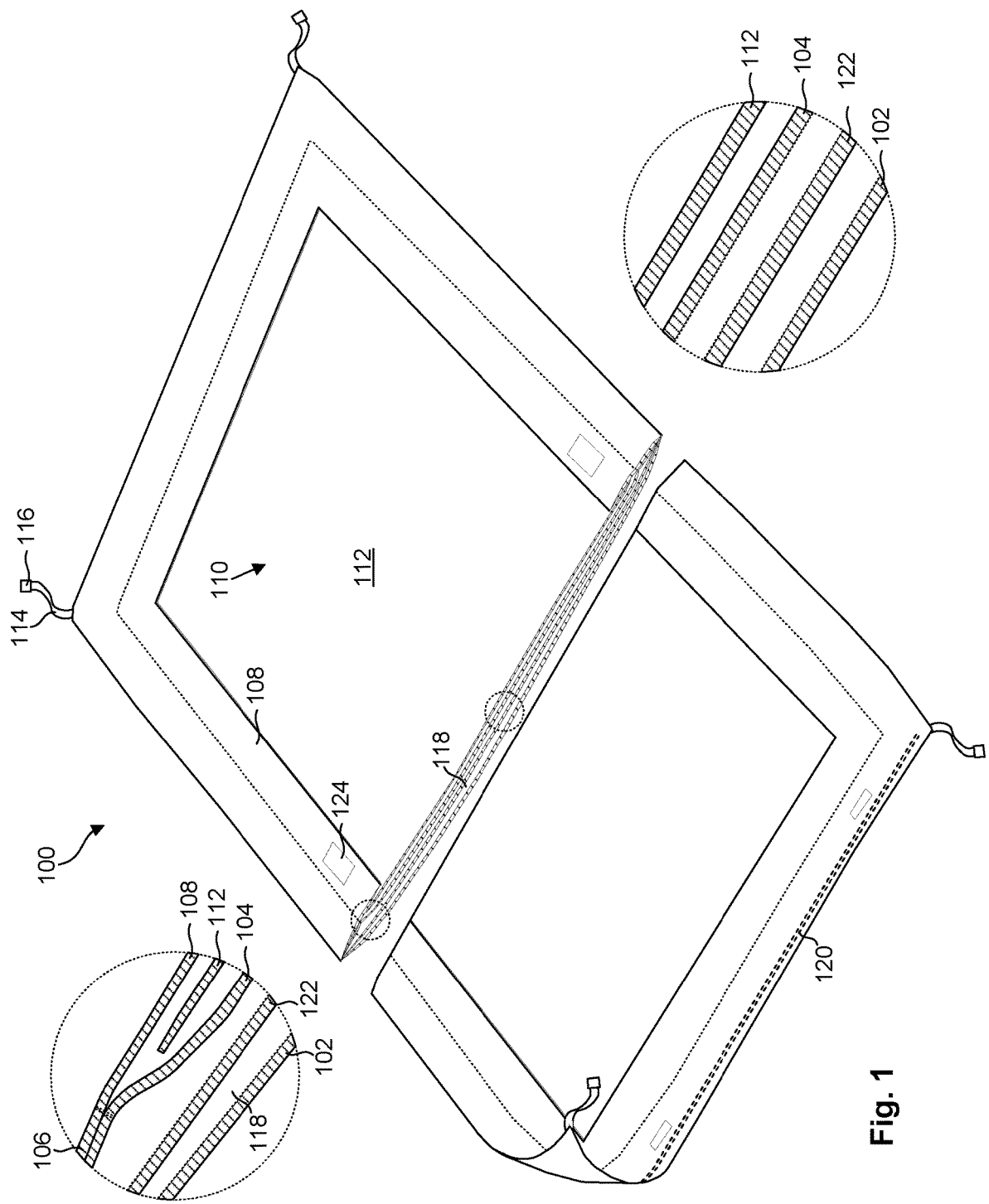
FIG. 1 is a top perspective view of an absorbent bed pad in accordance with the invention.

Referring to FIG. 1, bedwetting can be a serious nuisance for caregivers and affected individuals alike. While children may eventually outgrow the condition, in many cases bedwetting is a condition that must simply be tolerated for an extended period of time, and sometimes indefinitely. The time and labor needed to clean up after a bedwetting incident can be significant, in addition to the emotional toll and embarrassment it causes.

Disposable bed pads are often used as a way to facilitate fast and easy clean up. While considerably more convenient and inexpensive than regularly laundering cloth bedding, disposable bed pads are difficult to use discreetly as they are noisy and require effort to position properly. In addition, disposable bed pads tend to crumple easily under an individual's weight and movement, thereby reducing their effectiveness and causing discomfort to a user. Systems and methods in accordance with the present invention aim to address these problems to facilitate quick and easy clean-up while maintaining discreetness and user comfort.

Specifically, as shown in FIG. 1, in certain embodiments, an absorbent bed pad 100 in accordance with the present invention may include a bottom layer 102, a base layer 104, and an upper layer 106. At least a portion of the bottom layer 102 may include a roughened or substantially non-slip surface to prevent slippage of the absorbent bed pad 100 relative to a fitted sheet, mattress, or other structure or material thereunder.

An attachment mechanism may be used to further secure the absorbent bed pad 100 to an underlying structure or material. For example, in some embodiments, a strap 114 may be secured to one or more edges of the absorbent bed pad 100 and may extend substantially perpendicularly with respect to the edge from which it is attached. Each strap 114 may include a clasp, buckle, ring, slide, hook, or other fastener 116 attached to an end thereof. A mating fastener 116 may be attached to a corresponding strap 114 affixed or coupled to a mattress, fitted sheet, or other bedding material thereunder. In some embodiments, the mating fastener 116 may be attached to a corresponding strap 114 fit between the mattress and a box spring or bed frame. In this manner, the mating straps 114 may be easily joined for proper placement of the absorbent bed pad 100 relative to another sleeping surface, and may be released to facilitate quick and easy laundering or replacement.

The bottom layer 102, base layer 104, and upper layer 106 may be substantially congruent in shape and size, and may be substantially aligned with each other such that an outer periphery of the bottom layer 102 substantially corresponds to an outer periphery of each of the base layer 104 and the upper layer 106. The outer peripheries of each layer 102, 104, 106 may be secured or bonded to one another by quilting stitches 116, or via one or more fasteners, buttons, snaps, hook and loop fasteners, zippers, or other bonding or fastening mechanisms known to those in the art. In certain embodiments, two or more of the bottom layer 102, the base layer 104, and the upper layer 106 may be formed from a unitary piece of cloth.

The upper layer 106 may include a lip portion 108 that defines a central aperture 110 configured to receive an absorbent, removable pad 112. An outer periphery of the removable pad 112 may be substantially overlapped by the lip portion 108 to maintain the removable pad 112 in a substantially flat, stable position relative to each of the base layer 104 and the upper layer 106.

Optionally, one or more fastening mechanisms 124 may be coupled to the base layer 104 or lip portion 108 to further secure the removable pad 112 with respect to the adjacent layers 104, 106. A fastening mechanism 124 may include, for example, a button, snap, hook and loop fastener, adhesive, bonding material, or other such fastener known to those in the art. In some embodiments, the removable pad 112 may be disposable to facilitate quick and easy clean up.

At least one edge of the bottom layer 102 may include a releasable fastening mechanism 120 to provide access to an interior pocket 118 between the bottom layer 102 and the base layer 104. A releasable fastening mechanism 120 may include, for example, a zipper, buttons, snaps, hook and loop fasteners, or the like. The interior pocket 118 may include dimensions sufficient to accommodate a substantially liquid-impermeable insert layer 122. The liquid-impermeable insert layer 122 may be selectively inserted into or removed from the interior pocket 118 to provide an extra layer of protection to prevent liquids from passing through the absorbent bed pad 100.

Figure 2:
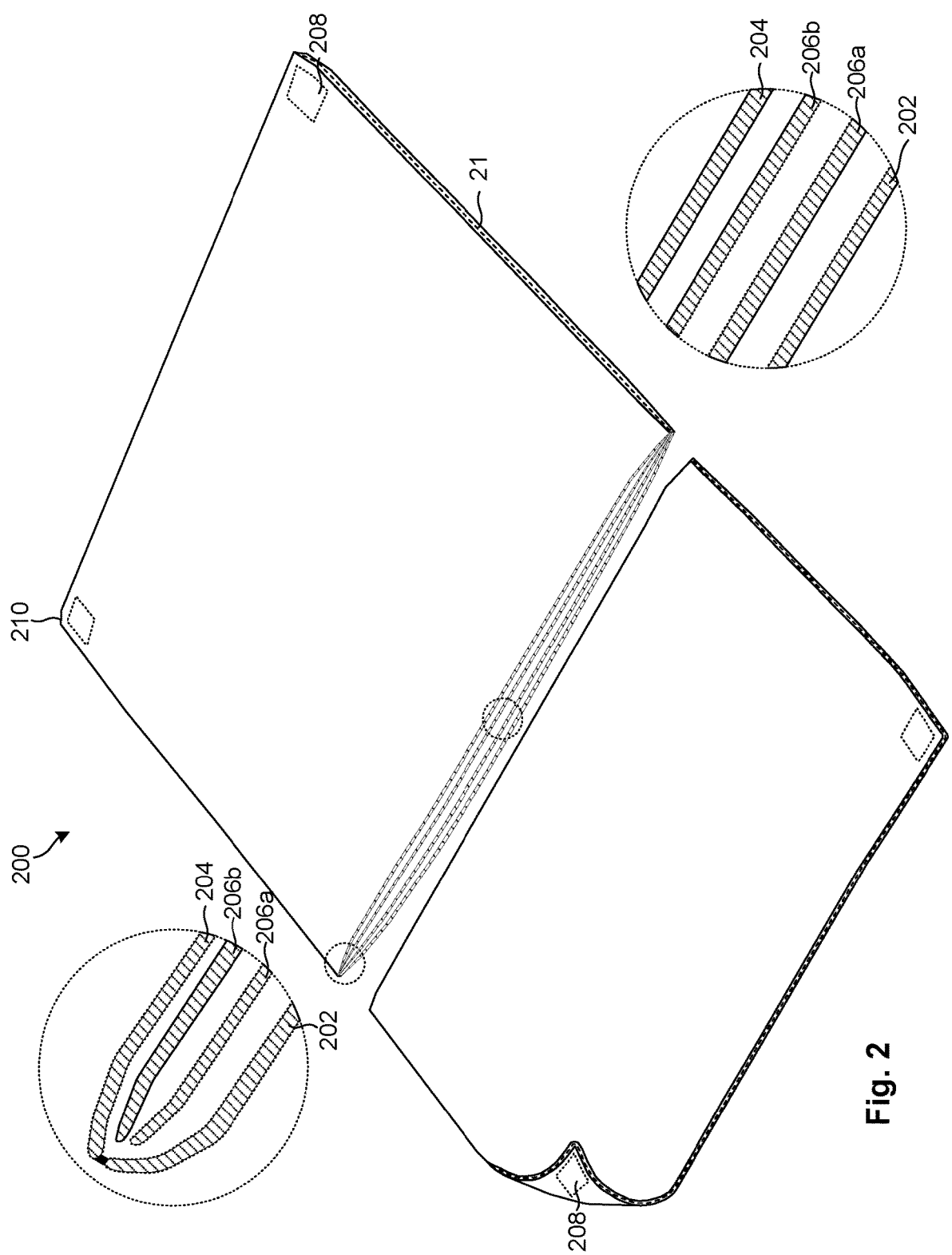
FIG. 2 is a perspective view of a weighted blanket in accordance with certain embodiments of the invention.

In addition to urinary incontinence, some users may suffer from other conditions or disabilities. For example, people that suffer from incontinence may also suffer from post-traumatic stress syndrome, autism, anxiety, or other such disabilities. In certain cases, a weighted blanked may be used to comfort those with such disabilities. FIG. 2 shows one example of a weighted blanket 200 that may be used to alleviate these disabilities.

As shown in FIG. 2, a weighted blanket 200 in accordance with the invention may include a bottom layer 202 and a top layer 204. The bottom layer 202 and the top layer 204 may be substantially congruent and aligned so that the top layer 204 is substantially on top of the bottom layer 202.

Each of the bottom and top layers 202, 204 may include fabrics or cloth selected for its ability to provide comfort through direct contact with a user. In certain embodiments, for example, the bottom and top layers 202, 204 may include substantially unique characteristics with respect to one another to enable a user to select either side for direct contact with their skin, depending upon their personal preference. In one embodiment, for example the bottom layer 202 may be fabricated from a high quality cotton sheet material to provide a cooling effect, while a top layer 204 may be fabricated from a fabric or material that is plush or soft to the touch to provide a warming effect. In other embodiments, the bottom layer 202 and top layer 204 may be fabricated from the same material.

The bottom layer 202 may be secured or bonded to the top layer 204 along at least one edge thereof. The bottom layer 202 may be secured to the top layer 204 by quilting stitches, or by one or more fasteners, buttons, snaps, hook and loop fasteners, zippers 212 (as shown), adhesive or bonding material, or other fastening mechanism known to those in the art. In some embodiments, the bottom layer 202 and top layer 204 may be secured to one another by way of, for example, a fastening mechanism 208 corresponding to least one corner 210 of the weighted blanket 200. A fastening mechanism 208 may include, for example, at least one button, snap, hook and loop fastener, adhesive or bonding material, or the like.

One or more intermediate layers 206a, 206b may be implemented between the bottom layer 202 and the top layer 204. Each of the intermediate layers 206a, 206b may include dimensions substantially corresponding to each of the bottom layer 202 and top layer 204. In this manner, each of the intermediate layers 206a, 206b may be substantially aligned with the bottom layer 202 and top layer 204 to reside therebetween.

In some embodiments, the intermediate layers 206a, 206b may be connected to each other and/or to the bottom layer 202 or top layer 204 by way of a fastening mechanism 208 attached to one or more corners 210. As described above, the fastening mechanism 208 may include at least one button, snap, hook and loop fastener, adhesive or bonding material, or the like. In some embodiments, the corners 210 of each of the intermediate layers 206a, 206b and/or bottom and top layers 202, 204 may not be fully attached to one another, thereby providing some pliability or flexibility to the weighted blanket 200 at the corners 210.

The intermediate layers 206a, 206b may be selectively added or removed from the weighted blanket 200 as desired to provide more or less weight. In some embodiments, the intermediate layers 206a, 206b may include fabrics or filler materials having varying weights and characteristics. In one embodiment, for example, intermediate layers 206a, 206b may include fabrics or materials selected exclusively for their weight characteristics without regard to whether their external surfaces are suitable or desirable for direct human contact.

In the above disclosure, reference has been made to the accompanying drawings, which form a part hereof, and in which is shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

The invention claimed is:

1. An apparatus for addressing urinary incontinence, the apparatus comprising:
  a base layer;
  an upper layer coupled to the base layer, wherein at least two adjacent outer edges of the upper layer are aligned with at least two adjacent outer edges of the base layer, the upper layer comprising a lip portion that is configured to overlap an outer periphery of a replaceable absorbent pad and thereby removably retain the replaceable absorbent pad in a stable position between the lip portion and the base layer, the lip portion further forming an aperture circumscribed within the base layer and extending centrally to expose the replaceable absorbent pad through the aperture.

2. The apparatus of claim 1, further comprising a liquid-impermeable layer configured to reside below the absorbent pad.

3. The apparatus of claim 2, further comprising a bottom layer below the base layer and forming a pocket between the bottom layer and the base layer.

4. The apparatus of claim 3, wherein the liquid-impermeable layer is configured to slide into and out of the pocket.

5. The apparatus of claim 4, further comprising a first fastening mechanism to fix the liquid-impermeable layer within the pocket.

6. The apparatus of claim 5, further comprising a zipper to open and close the pocket.

7. The apparatus of claim 1, further comprising a fastening mechanism to attach the replaceable absorbent pad to the base layer.

8. The apparatus of claim 1, further comprising an attachment mechanism to attach the apparatus to a bed.

9. The apparatus of claim 1, wherein the base layer and upper layer are liquid permeable.

10. The apparatus of claim 1, wherein the base layer and upper layer are fabricated from cloth.

\* \* \* \* \*